(12) United States Patent
Rasenack et al.

(10) Patent No.: US 9,156,835 B2
(45) Date of Patent: Oct. 13, 2015

(54) MICRONIZATION METHOD

(75) Inventors: Norbert Rasenack, Weil am Rhein (DE); Michael Walz, Bingen (DE); Michael Trunk, Ingelheim (DE); Hagen Graebner, Ingelheim (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 1788 days.

(21) Appl. No.: 12/096,308

(22) PCT Filed: Dec. 7, 2006

(86) PCT No.: PCT/EP2006/069450
§ 371 (c)(1),
(2), (4) Date: Jun. 25, 2009

(87) PCT Pub. No.: WO2007/068655
PCT Pub. Date: Jun. 21, 2007

(65) Prior Publication Data
US 2010/0215590 A1 Aug. 26, 2010

(30) Foreign Application Priority Data
Dec. 14, 2005 (DE) .................. 10 2005 059 602

(51) Int. Cl.
*A61K 9/14* (2006.01)
*C07D 451/10* (2006.01)
*A61K 9/16* (2006.01)
*A61K 31/439* (2006.01)

(52) U.S. Cl.
CPC ............. *C07D 451/10* (2013.01); *A61K 9/14* (2013.01); *A61K 9/16* (2013.01); *A61K 9/1682* (2013.01); *A61K 31/439* (2013.01)

(58) Field of Classification Search
CPC .......... A61K 9/14; A61K 9/16; A61K 9/1682
USPC .................................. 424/465–489
See application file for complete search history.

(56) References Cited

U.S. PATENT DOCUMENTS

| | | | |
|---|---|---|---|
| 5,308,596 A * | 5/1994 | Kotzian et al. | 423/333 |
| 6,777,423 B2 | 8/2004 | Banholzer et al. | |
| 6,908,928 B2 | 6/2005 | Banholzer et al. | |
| 7,309,707 B2 | 12/2007 | Bender et al. | |
| 7,642,268 B2 | 1/2010 | Bender et al. | |
| 2002/0169321 A1 | 11/2002 | Banholzer et al. | |
| 2003/0171586 A1 | 9/2003 | Banholzer et al. | |
| 2004/0002510 A1* | 1/2004 | Bender et al. | 514/291 |
| 2004/0087793 A1 | 5/2004 | Banholzer et al. | |
| 2004/0132759 A1* | 7/2004 | Konetzki et al. | 514/291 |
| 2006/0075930 A1* | 4/2006 | Wang et al. | 106/638 |
| 2006/0257491 A1* | 11/2006 | Morton et al. | 424/489 |
| 2007/0015785 A1 | 1/2007 | Bender et al. | |

FOREIGN PATENT DOCUMENTS

| | | | |
|---|---|---|---|
| WO | 0230928 A1 | 4/2002 | |
| WO | 03078429 A1 | 9/2003 | |
| WO | 2004084897 A1 | 10/2004 | |

OTHER PUBLICATIONS

Godet-Morand, Laurence, et al; Talc Grinding in an Opposed Air Jet Mill: Start-Up, Product Quality and Production Rate Optimization; Powder Technology (2002) vol. 128 pp. 306-313.
International Search Report for PCT/EP2006/069450 mailed Feb. 28, 2007.

* cited by examiner

*Primary Examiner* — Michael G Hartley
*Assistant Examiner* — Micah-Paul Young
(74) *Attorney, Agent, or Firm* — Michael P. Morris; Wendy A. Petka

(57) ABSTRACT

The invention relates to a method for producing a micronized, virtually anhydrous form of (1α,2β,4β,5α,7β)-7-[(hydroxydi-2-thienylacetyl)oxy]-9,9-dimethyl-3-oxa-9-azoniatricyclo[3.3.1.0$^{2,4}$]nonane bromide, said form per se, and the use thereof for producing a medicament, especially a medicament having an anticholinergic effect.

20 Claims, 1 Drawing Sheet

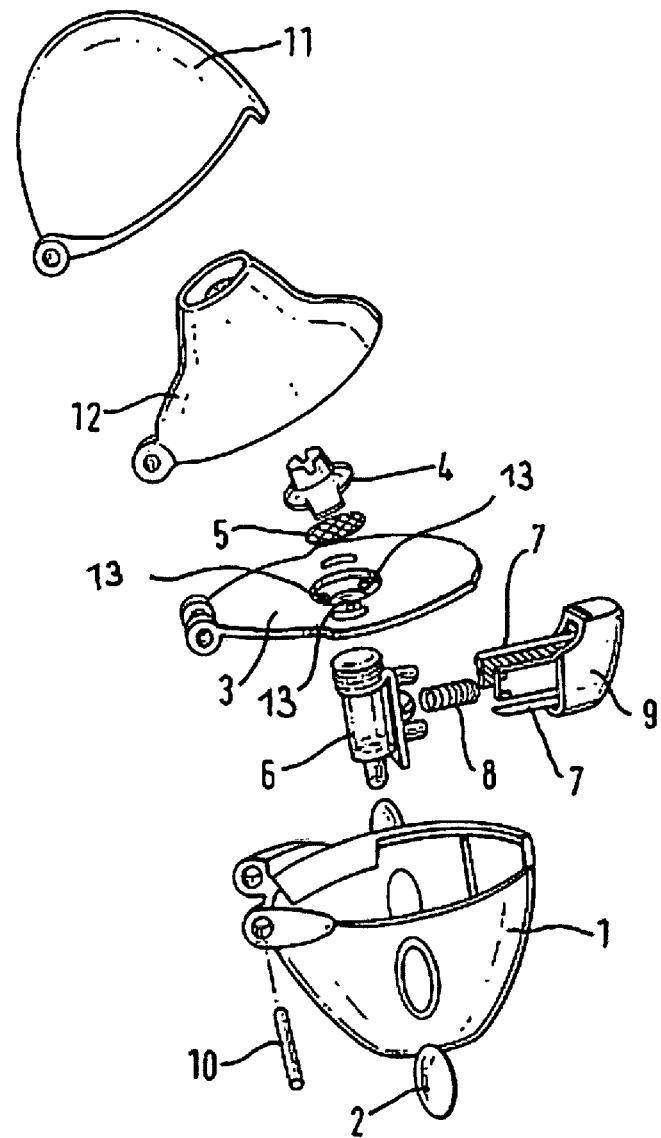

MICRONIZATION METHOD

RELATED APPLICATIONS

This application is a 371 of International Application No. PCT/EP2006/069450, filed Dec. 7, 2006, which claims priority to German Patent Application No. 10 2005 059 602, filed Dec. 14, 2005, the contents of which are incorporated herein by reference in their entirety.

FIELD OF THE INVENTION

The invention relates to a process for preparing a micronised anhydrous form of (1α,2β,4β,5α,7β)-7-[(hydroxydi-2-thienylacetyl)oxy]-9,9-dimethyl-3-oxa-9-azoniatricyclo [3.3.1.0$^{2,4}$]nonane-bromide, the form as such, as well as the use thereof for preparing a medicament, particularly for preparing a medicament with an anticholinergic activity.

BACKGROUND TO THE INVENTION

The compound (1α,2β,4β,5α,7β)-7-[(hydroxydi-2-thienylacetyl)oxy]-9,9-dimethyl-3-oxa-9-azoniatricyclo [3.3.1.0$^{2,4}$]nonane-bromide is known from European Patent Application EP 418 716 A1 and has the following chemical structure:

(I)

The compound has valuable pharmacological properties and is known by the name tiotropium bromide (BA679). Tiotropium bromide is a highly effective anticholinergic and can therefore provide a therapeutic benefit in the treatment of asthma or COPD (chronic obstructive pulmonary disease).

Tiotropium bromide is preferably administered by inhalation. Suitable inhalable powders packed into appropriate capsules (inhalettes) and administered by corresponding powder inhalers may be used. Alternatively, it may be administered by inhalation using suitable inhalable aerosols. These also include powdered inhalable aerosols which contain, for example, HFA134a, HFA227 or mixtures thereof as propellant gas.

With regard to the inhalative administration of tiotropium bromide, it is essential to provide the active substance in a finely divided (or micronised) form. The active substance preferably has an average particle size of 0.5 to 10 µm, preferably 1 to 6 µm, particularly preferably from 1.5 to 5 µm.

The above-mentioned particle sizes are generally achieved by grinding (so-called micronisation) of the active substance. Since it is important to avoid, as far as possible, any degradation of the active substance of the medicament as a result of the grinding process, in spite of the hard conditions required while the process is taking place, high stability of the active substance vis-á-vis the grinding operation is an absolute necessity. It must be borne in mind that in the course of the grinding process there may in certain circumstances be changes to the solid characteristics of the active substance which may affect the pharmacological properties of the medicament formulation to be administered by inhalation.

Methods of micronising pharmaceutically active substances, including tiotropium bromide, are known per se in the prior art. Thus, for example, WO 03/078429 discloses a method of preparing micronised crystalline tiotropium bromide monohydrate.

The objective of the present invention is to provide a process which allows virtually anhydrous micronised tiotropium bromide that meets the requirements stated hereinbefore to be produced economically.

BRIEF DESCRIPTION OF THE FIGURES

FIG. 1: Inhaler that may be used to administer inhalable powder according to the invention

DETAILED DESCRIPTION OF THE INVENTION

The above mentioned objectives are achieved by means of the process described below.

The present invention relates to a process for preparing virtually anhydrous tiotropium bromide in micronised form, characterised in that crystalline tiotropium bromide monohydrate is comminuted in a gas jet mill, wherein the tiotropium bromide monohydrate particles are comminuted in a fluidised powder bed.

The "virtually anhydrous tiotropium bromide in micronised form" mentioned above is also optionally referred to within the scope of the present invention as virtually anhydrous micronised tiotropium bromide, or simply as micronised tiotropium bromide.

Within the scope of the present invention the expression "virtually anhydrous" denotes crystalline tiotropium bromide that has a water content of ≤1.5%, preferably ≤1.2%, more preferably ≤1%. Particularly preferably the term "virtually anhydrous" denotes a crystalline tiotropium bromide which is characterised by a water content of ≤0.8%. The water content is determined within the scope of the present invention by biamperometric titration according to Karl Fischer. More details of this can be found in the experimental descriptions of the invention.

Within the scope of the present invention the term tiotropium bromide "in micronised form" refers to tiotropium bromide which has a characteristic particle size $X_{50}$ of between 1.0 µm and 3.5 µm, preferably between 1.1 µm and 3.3 µm, most preferably between 1.2 µm and 3.0 µm and $Q_{(5.8)}$ of more than 60%, preferably more than 70%, most preferably more than 80%. The characteristic value $X_{50}$ denotes the median value of the particle size, below which fall 50% of the quantity of particles, based on the volume distribution of the individual particles. The characteristic value $Q_{(5.8)}$ corresponds to the quantity of particles below 5.8 µm, based on the volume distribution of the particles. The particle sizes were determined within the scope of the present invention by laser diffraction (Fraunhofer diffraction). More detailed information on this subject can be found in the experimental descriptions of the invention.

Within the scope of the present invention the term crystalline tiotropium bromide monohydrate denotes the crystalline modification of tiotropium bromide monohydrate which is characterised by an endothermic maximum at 230±5° C. at a heating rate of 10K/min, when thermally analysed by DSC.

This crystalline modification can also be described by an IR spectrum that has bands inter alia at wavelengths 3570, 3410, 3105, 1730, 1260, 1035 and 720 cm$^{-1}$ and is further characterised by a simple monoclinic cell with the following dimensions: a=18.0774 Å, b=11.9711 Å, c=9.9321 Å, β=102.691°, V=2096.96 Å$^3$ (determined by monocrystalline X-ray structural analysis). Processes for preparing this modification and experimental data for determining the above-mentioned characteristics are disclosed in WO 02/30928, to which reference is made in this respect. A process for preparing crystalline tiotropium bromide monohydrate from tropenol can also be found in WO 02/051840. Crystalline tiotropium bromide monohydrate obtainable by the above methods known in the art is used in the process according to the invention. The particle size of the crystalline tiotropium bromide monohydrate used in the process is fundamentally of secondary importance to the feasibility of the process according to the invention. Normally, crystalline tiotropium bromide monohydrate which has a mean particle size in the range from about 50-1000 μm, preferably about 100-800 μm, particularly preferably about 200-600 μm, is used in the process according to the invention.

The particle sizes are determined within the scope of the present invention by laser diffraction (Fraunhofer diffraction). More detailed information on this subject can be found in the experimental descriptions of the invention.

Within the scope of the present invention the term gas jet mill denotes a mill in which particles are ground by high particle acceleration produced by the expanding grinding gas as a result of friction, collision and impact. Besides this grinding function, gas jet mills also have a sifting function. This sifting function separates small particles from large ones, the small particles enter the product collector while the large particles are subjected to further grinding until they are also fine enough to pass through the sifter.

Within the scope of the present invention the grinding has may be air, dehumidified air, fractionated air, noble gases, nitrogen or mixtures of the above. Fractionated air is preferred, most preferably nitrogen. By fractionated air is meant, within the scope of the present invention, a gas that contains constituents of the air in concentrated purified form. Nitrogen of quality grade 5.0 is particularly suitable. This quality grade describes the purity, while the grade 5.0 indicates a purity of >99.999% (incl. noble gases) with a content of subsidiary ingredients of ≤3 ppm oxygen, ≤5 ppm water.

The gas jet mills that are used within the scope of the present invention are also characterised in that the particles to be micronised are comminuted in a fluidised bed of powder. This bed of powder forming within the grinding chamber is also referred to in the literature as a fluidised bed, or fluid bed. As in other gas jet mills, the acceleration of the particles takes place in the free flow but comminution is carried out in single current and in countercurrent. The mills used within the scope of the present invention are therefore also referred to as a countercurrent mills or fluidised bed countercurrent mills. In the grinding chamber a fluidised bed of powder is formed on which the reduction in particle size takes place as a result of collision, impact and friction. The grinding jets are directed towards one another and meet centrally at one point. The screening function is provided separately by means of a freely movable screening wheel that can be actuated separately. The speed of rotation of the screening wheel determines the size of particles that can pass through the screening wheel. The coarse particles are rejected and fed back into the grinding process in the grinding chamber. The fine particles pass through the screening wheel and enter the product container.

The countercurrent mill is a suitable apparatus for comminuting substances. The particle size of the product may be controlled by means of the machine parameters, as known from the prior art (cf. Godet-Morand, L. et al., Powder Technology 128 (2002) 306-313; Heng, P. W. S. et al., S. T. P. Pharma Sciences 10 (1) 445-451 (2000)).

In the countercurrent mills that are used according to the invention the essential variable process parameters are grinding pressure, nozzle size and screening wheel speed. Within the scope of the present invention the grinding pressure is usually adjusted to a value of 2-10 bar, preferably 3-8 bar, particularly preferably 4-6 bar. The material for grinding is fed into the air jet mill using a suitable metering device (for example K-Tron (K-Tron GmbH, Gelnhausen, Germany). Within the scope of the present invention it is particularly preferable to use countercurrent mills that are characterised by 3 grinding jets directed towards one another, each having a jet diameter of 1.3 to 2.5 mm, preferably from 1.6-2.2 mm, particularly preferably about 1.9 mm. By the nozzle diameter is also meant, within the scope of the present invention, the internal diameter of the grinding jet.

Within the scope of the present invention a screening wheel speed of 5000-22000, preferably 10000-20000, particularly preferably 14000-19000, particularly 16000-18000 has proved suitable. The screening wheel speeds stated above are in each case revolutions per minute.

For example and without restricting the subject matter of the invention thereto, the following apparatus has proved suitable as one possible embodiment of a countercurrent mill that may be used according to the invention: Opposed jet-mill AFG 100 (Hosokawa-Alpine, Augsburg, Germany)

Surprisingly it was found that using the process according to the invention anhydrous modification of the tiotropium bromide in micronised form occurs directly. This is inter alia characterised in that in an X-ray powder diagram it has inter alia the characteristic values d=5.66 Å; 5.03 Å and 3.99 Å.

The invention also relates to virtually anhydrous tiotropium bromide which can be obtained by means of the process mentioned above and is characterised by the above-mentioned features.

In another aspect the present invention relates to the use of the virtually anhydrous micronised tiotropium bromide obtained according to the invention as a medicament, on account of the pharmaceutical activity of the micronised product according to the invention.

In another aspect the present invention relates to inhalable powder characterised in that they contain an amount of virtually anhydrous micronised tiotropium bromide according to the invention.

In view of the anticholinergic activity of tiotropium bromide a further aspect of the present invention relates to the use of the virtually anhydrous micronised tiotropium bromide according to the invention for preparing a pharmaceutical composition for the treatment of diseases in which the administration of an anticholinergic may confer a therapeutic benefit. Preferably it is used to prepare a medicament for the treatment of asthma or COPD.

The virtually anhydrous micronised tiotropium bromide which may be obtained according to the invention is exceptionally suitable for the preparation of pharmaceutical formulations. Particularly preferably it may be used to prepare inhalable powders.

Accordingly, the present invention relates to inhalable powders containing at least about 0.029%, preferably less than 4.81%, particularly preferably less than 2.89% of the virtually anhydrous micronised tiotropium bromide which may be obtained according to the above process in admixture with a physiologically acceptable excipient and optionally other excipients or active substances. In mixtures with other substances the virtually anhydrous micronised preparation obtained by the process described above may be characterised by particular properties that influence the properties of the formulation, such as for example improved stability, e.g. improved chemical and physicochemical stability.

Examples of physiologically acceptable excipients which may be used to prepare the inhalable powders containing the micronised preparation according to the invention include, for example, monosaccharides (e.g. glucose or arabinose), disaccharides (e.g. lactose, saccharose, maltose or trehalose), oligo- and polysaccharides (e.g. dextrane), polyalcohols (e.g. sorbitol, mannitol, xylitol), salts (e.g. sodium chloride, calcium carbonate) or mixtures of these excipients with one another. Preferably, mono- or disaccharides are used, while the use of lactose, glucose or trehalose, preferably lactose or glucose is preferred, particularly, but not exclusively, in the form of their hydrates. For the purposes of the invention, lactose is the particularly preferred excipient, while lactose monohydrate is most particularly preferred.

Preferred according to the invention are inhalable powders that contain about 0.049 to about 0.96%, preferably about 0.096 to about 0.77%, particularly preferably about 0.19 to about 0.48% of virtually anhydrous micronised tiotropium bromide, which may be obtained by the process described hereinbefore and has the distinguishing characteristics of the micronised preparation obtainable according to the invention.

The pharmaceutical compositions or inhalable powders that contain the virtually anhydrous micronised tiotropium bromide obtainable according to the invention may further be characterised in that the excipient has an average particle size of 10-50 μm, a 10% fine content of 0.5 to 6 μm and a specific surface area of 0.1 to 2 $m^2/g$.

By the average particle size is meant here the 50% value of the volume distribution measured using a laser diffractometer by the dry dispersion method. Analogously, the 10% fine content in this instance refers to the 10% value of the volume distribution measured using a laser diffractometer. In other words, for the purposes of the present invention, the 10% fine content denotes the particle size below which 10% of the quantity of particles is found (based on the volume distribution).

By specific surface area is meant, for the purposes of the invention, the mass-specific powder surface area, calculated from the $N_2$ absorption isotherm which is observed at the boiling point of liquid nitrogen (method of Brunauer, Emmett and Teller).

The percentages given within the scope of the present invention are always percent by weight, unless specifically stated to the contrary.

In particularly preferred inhalable powders the excipient is characterised by an average particle size of 12 to 35 μm, more preferably 13 to 30 μm. Also particularly preferred are those inhalable powders wherein the 10% fine content is about 1 to 4 μm, preferably about 1.5 to 3 μm.

Alternative pharmaceutical compositions which contain the virtually anhydrous tiotropium bromide according to the invention are further characterised in that the excipient consists of a mixture of coarser excipient with an average particle size of 17 to 50 μm, most preferably 20 to 30 μm, and finer excipient with an average particle size of 2 to 8 μm, most preferably 3 to 7 μm. Preferred powders for inhalation are those wherein the proportion of finer excipient constitutes 3 to 15%, most preferably 5 to 10% of the total amount of excipient.

When reference is made to a mixture within the scope of the present invention, this always means a mixture obtained by mixing together clearly defined components. Accordingly, when an excipient mixture of coarser and finer excipients is mentioned, this can only denote mixtures obtained by mixing a coarser excipient component with a finer excipient component.

The coarser and finer excipient fractions may consist of chemically identical or chemically different substances, while inhalable powders in which the coarser excipient fraction and the finer excipient fraction consist of the same chemical compound are preferred.

For administering the inhalative powders according to the invention using powder-containing capsules it is preferable to use capsules having a shell made of gelatine, cellulose derivatives, starch, starch derivatives, chitosan or synthetic plastics.

If gelatine is used as the capsule material, it may be used in admixture with other additives selected from among polyethyleneglycol (PEG), preferably PEG 3350, glycerol, sorbitol, propyleneglycol, PEO-PPO block copolymers and other polyalcohols and polyethers. Within the scope of the present invention gelatine is used particularly preferably in admixture with PEG, preferably PEG 3350. A gelatine capsule according to the invention preferably contains PEG in an amount of 1-10% (wt.-%), preferably 3-8%. Particularly preferred gelatine capsules contain PEG in an amount of 4-6%, a PEG content of about 5% being most preferred according to the invention.

If cellulose derivatives are used as the capsule material, it is preferable to use hydroxypropylmethylcellulose, hydroxypropylcellulose, methylcellulose, hydroxymethylcellulose and hydroxyethylcellulose. In this case, hydroxypropylmethylcellulose (HPMC), particularly preferably HPMC 2910 is used as the capsule material.

If synthetic plastics are used as the capsule material, these are preferably selected according to the invention from among polyethylene, polycarbonate, polyester, polypropylene and polyethylene terephthalate. Particularly preferred synthetic plastics for the capsules for inhalation according to the invention are polyethylene, polycarbonate or polyethylene terephthalate. If polyethylene is used as one of the particularly preferred capsule materials according to the invention, polyethylene with a density of between 900 and 1000 $kg/m^3$, preferably from 940-980 $kg/m^3$, particularly preferably about 960-970 $kg/m^3$ is preferably used (high-density polyethylene).

The synthetic plastics according to the invention may be processed in various ways using manufacturing methods known in the art. Injection moulding of the plastics is preferred according to the invention. Injection moulding without the use of mould release agents is particularly preferred. This method of production is well defined and is characterised by being particularly reproducible.

In another aspect the present invention relates to the abovementioned capsules which contain the abovementioned inhalable powders according to the invention. These capsules may contain about 1 to 20 mg, preferably about 3 to 15 mg, most preferably about 4 to 12 mg of inhalable powder. Preferred formulations according to the invention contain 4 to 6 mg of inhalable powder. Of equivalent importance according to the invention are capsules for inhalation which contain the formulations according to the invention in an amount of from 8 to 12 mg.

Moreover, pharmaceutical compositions which contain the virtually anhydrous tiotropium bromide according to the invention may be characterised in that they contain further active substances, in addition to the micronised virtually anhydrous tiotropium bromide obtainable by the process according to the invention.

These active substances are preferably selected from among the betamimetics, corticosteroids, PDE4-inhibitors, LTD4-antagonists, EGFR-inhibitors, dopamine agonists, H1-antihistamines or PAF-antagonists.

Examples of betamimetics which may be used are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1,4]oxazin-3-one, 6-hydroxy-8-{1-hydroxy-2-[2-(ethyl 4-phenoxy-acetate)-1,1-dimethyl-ethylamino]-ethyl}-4H-benzo[1,4]oxazin-3-one, 6-hydroxy-8-{1-hydroxy-2-[2-(4-phenoxy-acetic acid)-1,1-dimethyl-ethylamino]-ethyl}-4H-benzo[1,4]oxazin-3-one, 8-{2-[1,1-dimethyl-2-(2,4,6-trimethylphenyl)-ethylamino]-1-hydroxy-ethyl}-6-hydroxy-4H-benzo[1,4]oxazin-3-one, 6-hydroxy-8-{1-hydroxy-2-[2-(4-hydroxy-phenyl)-1,1-dimethyl-ethylamino]-ethyl}-4H-benzo[1,4]oxazin-3-one, 6-hydroxy-8-{1-hydroxy-2-[2-(4-isopropyl-phenyl)-1,1-dimethyl-ethylamino]-ethyl}-4H-benzo[1,4]oxazin-3-one, 8-{2-[2-(4-ethyl-phenyl)-1,1-dimethyl-ethylamino]-1-hydroxy-ethyl}-6-hydroxy-4H-benzo[1,4]oxazin-3-one, 8-{2-[2-(4-ethoxy-phenyl)-1,1-dimethyl-ethylamino]-1-hydroxy-ethyl}-6-hydroxy-4H-benzo[1,4]oxazin-3-one, 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1,4]oxazin-3-one and 1-(4-ethoxy-carbonylamino-3-cyano-5-fluorophenyl)-2-(tert.-butylamino)ethanol, optionally in the form of the racemates, enantiomers, diastereomers thereof and optionally in the form of the pharmacologically acceptable acid addition salts, solvates or hydrates thereof. Preferred according to the invention are the acid addition salts of the betamimetics selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of corticosteroids which may be used are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, ST-26, (S)-fluoromethyl 6,9-difluoro-17-[(2-furanylcarbonyl)oxy]-11-hydroxy-16-methyl-3-oxo-androsta-1,4-diene-17-carbothionate, (S)-(2-oxo-tetrahydro-furan-3S-yl)6,9-difluoro-11-hydroxy-16-methyl-3-oxo-17-propionyloxy-androsta-1,4-diene-17-carbothionate and etiprednol-dichloroacetate, optionally in the form of the racemates, enantiomers or diastereomers thereof and optionally in the form of the salts and derivatives, solvates and/or hydrates thereof. Any reference to steroids includes a reference to any salts or derivatives, hydrates or solvates thereof that may exist. Examples of possible salts and derivatives of the steroids may be: alkali metal salts, such as for example sodium or potassium salts, sulphobenzoates, phosphates, isonicotinates, acetates, propionates, dihydrogen phosphates, palmitates, pivalates or furoates.

Examples of PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370, N-(3,5-dichloro-1-oxo-pyridin-4-yl)-4-difluoromethoxy-3-cyclopropylmethoxybenzamide, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-14], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers, diastereomers thereof and optionally in the form of the pharmacologically acceptable acid addition salts, solvates or hydrates thereof. Preferred according to the invention are the acid addition salts of the PDE4-inhibitors selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321, 1-(((R)-3-(2-(6,7-difluoro-2-quinolinyl)ethenyl)phenyl)-3-(2-(2-hydroxy-2-propyl)phenyl)thio)-methylcyclopropane-acetic acid, 1-(((1R)-3(3-(2-(2.3-dichlorothieno[3,2-b]pyridin-5-yl)-(E)-ethenyl)phenyl)-3-(2-(1-hydroxy-1-methylethyl)phenyl)-propyl)thio)methyl)

cyclopropaneacetic acid and [2-[[2-(4-tert-butyl-2-thiazolyl)-5-benzofuranyl]oxymethyl]phenyl]acetic acid, optionally in the form of the racemates, enantiomers, diastereomers thereof and optionally in the form of the pharmacologically acceptable acid addition salts, solvates or hydrates thereof. Preferred according to the invention are the acid addition salts of the LTD4-antagonists selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may possibly be capable of forming are meant for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

Examples of EGFR-inhibitors which may be used are preferably compounds selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropylmethoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6.7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino]-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino]-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxyquinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethane-sulphonylamino-cyclohexan-1-yloxy)-7-methoxy-quinazoline, 4-[(3-chloro-4-fluoro-phenyl)amino]-6-(1-methane-sulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline and 4-[(3-chloro-4-fluoro-phenyl)amino]-6-(1-cyano-piperidin-4-yloxy)-7-methoxy-quinazoline, optionally in the form of the racemates, enantiomers, diastereomers thereof and optionally in the form of the pharmacologically acceptable acid addition salts, solvates or hydrates thereof. Preferred according to the invention are the acid addition salts of the EGFR inhibitors selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of dopamine agonists which may be used are preferably compounds selected from among bromocriptin, cabergolin, alpha-dihydroergocryptin, lisurid, pergolid, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. Preferred according to the invention are the acid addition salts of the dopamine agonists selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of H1-antihistamines which may be used are preferably compounds selected from among epinastine, cetirizine, azelastin, fexofenadin, levocabastin, loratadine, mizolastin, ketotifen, emedastin, dimetinden, clemastin, bamipin, cexchlorpheniramine, pheniramin, doxylamine, chlorophenoxamine, dimenhydrinate, diphenhydramine, promethazine, ebastin, desloratidine and meclozine, optionally in the form of the racemates, enantiomers, diastereomers thereof and optionally in the form of the pharmacologically acceptable acid addition salts, solvates or hydrates thereof. Preferred according to the invention are the acid addition salts of the H1-antihistamines selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of PAF-antagonists which may be used are preferably compounds selected from among 4-(2-chlorophenyl)-9-methyl-2-[3(4-morpholinyl)-3-propanon-1-yl]-6H-thieno-[3.2]-[1.2.4]triazolo[4.3-a][1,4]diazepines and 6-(2-chlorophenyl)-8.9-dihydro-1-methyl-8-[(4-morpholinyl)carbonyl]-4H,7H-cyclo-penta-[4,5]thieno-[3,2-f][1.2.4]triazolo[4.3-a][1,4]diazepines, optionally in the form of the racemates, enantiomers, diastereomers thereof and optionally in the form of the pharmacologically acceptable acid addition salts, solvates or hydrates thereof. Preferred according to the invention are the acid addition salts of the PAF-antagonists selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Inhalable powders which may contain one or more of the above-mentioned additional active substances, besides the virtually anhydrous micronised tiotropium bromide, may be obtained analogously to preparation methods known in the art. Reference may be made for example to the disclosure of International Patent Applications WO 02/30390, WO 03/017970 or WO 03/017979.

The inhalable powders containing the micronised preparation according to the invention may be administered for example using inhalers which deliver a single dose from a supply using a measuring chamber as described in U.S. Pat. No. 4,570,630A, for example, or by other means as described in DE 36 25 685 A for example. Preferably, however, the inhalable powders are packed into capsules (to form so-called inhalettes), which are used in inhalers as described for example in WO 94/28958.

The present invention also relates to an inhalation kit consisting of one or more of the above capsules characterised by a content of inhalable powder according to the invention in conjunction with the inhaler according to FIG. 1.

Particularly preferably the capsules containing the inhalable powder according to the invention are administered using an inhaler as shown in FIG. 1.

This inhaler is characterised by a housing 1 containing two windows 2, a deck 3 in which there are air inlet ports and which is provided with a screen 5 secured via a screen housing 4, an inhalation chamber 6 connected to the deck 3 on which there is a push button 9 provided with two sharpened pins 7 and movable counter to a spring 8, and a mouthpiece 12 which is connected to the housing 1, the deck 3 and a cover 11 via a spindle 10 to enable it to be flipped open or shut and airholes 13 for adjusting the flow resistance.

The inhalable powders containing the micronised tiotropium bromide according to the invention are characterised by an exceptional degree of homogeneity in terms of single dose metering accuracy. This is in the region of <8%, preferably <6%, most preferably <4%.

The following, detailed experimental descriptions serve to illustrate the present invention still further without limiting the scope of the invention to the embodiments described by way of example hereinafter.

EXPERIMENTAL SECTION

A) Characterisations and Methods of Measurement

A.1) Characterisation of the Virtually Anhydrous Micronised Tiotropium Bromide

The virtually anhydrous micronised tiotropium bromide obtained by the above method was investigated further by X-ray powder diffractometry.

The X-ray powder diffractogram was recorded within the scope of the present invention using a Stoe & Cie Stadi P X-Ray Powder Diffractometer, OED Position Sensitive Detector; CuKα—radiation; 40 kV/40 mA; Monochromator: Germanium; 1.5406Å; Transmission method; Software package Powdat Table 1 below shows the characteristic peaks and standardised intensities.

TABLE 1

| d [Å] | Intensity [%] |
|---|---|
| 10.05 | 46.30 |
| 7.52 | 39.87 |
| 6.79 | 28.41 |
| 6.50 | 17.50 |
| 6.28 | 35.03 |
| 5.96 | 30.59 |
| 5.78 | 13.78 |
| 5.66 | 100.00 |
| 5.37 | 26.01 |
| 5.26 | 45.06 |
| 5.15 | 19.88 |
| 5.03 | 85.00 |
| 4.92 | 15.53 |
| 4.83 | 8.68 |
| 4.73 | 23.69 |
| 4.52 | 34.07 |
| 4.34 | 35.63 |
| 4.26 | 9.39 |
| 4.13 | 16.35 |
| 4.06 | 8.90 |
| 3.99 | 51.41 |
| 3.90 | 11.56 |
| 3.84 | 21.49 |
| 3.76 | 35.19 |
| 3.69 | 41.38 |
| 3.59 | 27.74 |
| 3.54 | 29.64 |
| 3.43 | 30.28 |
| 3.30 | 42.77 |
| 3.15 | 14.26 |
| 3.06 | 21.37 |
| 3.00 | 6.28 |
| 2.95 | 16.87 |
| 2.89 | 22.11 |
| 2.84 | 30.20 |
| 2.72 | 9.82 |
| 2.61 | 9.54 |
| 2.52 | 9.13 |
| 2.50 | 9.13 |
| 2.46 | 8.22 |
| 2.41 | 6.85 |
| 2.37 | 8.49 |
| 2.30 | 7.92 |

A.2) Determining the Water Content by the Karl-Fischer Method (Tiotropium Bromide)

| | |
|---|---|
| Titrator | 701 KF-Titrino with 703 Ti-Stand (Metrohm) with double platinum electrode; biamperometric titration |
| Calibrating substance: | Disodium tartrate dihydrate (e.g. Riedel de Haen; 15.66% water content) |
| Titrant: | Karl Fischer reagent p.a. (e.g. J. T. Baker; stabilised solution for electrochemical titration) |
| Solvent: | methanol p.a. (e.g. J. T. Baker) |

Method of Measurement:

| | |
|---|---|
| Sample quantity: | approx. 300 mg |
| Stirring time: | 60 s |

The stirring time before the start of titration serves to ensure that the sample is fully dissolved.

The water content of the sample is calculated by the apparatus in percent and the result is given.

A.3) Determination of Particle Size by Laser Diffraction (Fraunhofer Diffraction)

Method of Measurement:
In order to determine the particle size the powder is fed into a laser diffraction spectrometer using a dispersing unit.

| | |
|---|---|
| Measuring equipment: | Laser diffraction spectrometer (HELOS), Sympatec |
| Software: | WINDOX Version 4.2/ |
| Dispersing unit: | RODOS/Dispersing pressure: 3.0 bar |

Equipment Parameters:

| | |
|---|---|
| Detector: | Multielement detector (31 semicircular rings) |
| Method: | Air dispersion |
| Focal length: | 100 mm |
| Measuring range: | RS 0.5/0.9-175 μm |
| Evaluation mode: | HRLD mode |

Rodos Dry Disperser:

| | |
|---|---|
| Injector: | 4 mm |
| Pressure: | 3 bar |
| Injector underpressure: | maximum (~100 mbar) |
| Suction: | Nilfilsk (run time 5 s) |
| Metering device: | Vibri |
| Delivery rate: | 40% (manual increase to 100%) |
| Bed height: | 2 mm |
| Number of revolutions: | 0 |

A.4) Determining the Specific Surface (Multipoint B.E.T. Method)

Method of Measurement:
The specific surface is determined by exposing the powder sample to a nitrogen/helium atmosphere at different pressures. Cooling the sample causes the nitrogen molecules to be condensed on the surface of the particles. The quantity of condensed nitrogen is determined by means of the change in the thermal heat conductivity of the nitrogen/helium mixture and the surface of the sample is calculated by means of the surface nitrogen requirement. Using this value and the weight of the sample, the specific surface is calculated.
Equipment and Materials:

| | |
|---|---|
| Measuring equipment: | Multi-Point-BET; Micromeretics TriStar 3000 |
| Heater: | VacPrep; Micromeretics |
| Measuring and drying gas: | nitrogen (5.0)/helium (4.6) 70/30, Messer Griesheim |
| Refrigerant: | liquid nitrogen |

B) Examples

B.1) Preparation of the Virtually Anhydrous Micronised Tiotropium Bromide

The countercurrent mill AFG100 (Hosokawa-Alpine, Augsburg, Germany) is used for the micronisation according to the Examples described below.

In each case 500 g of tiotropium bromide monohydrate with an average particle size of 450 μm are micronised in the AFG100 countercurrent mill under the following conditions:

a) 4.0 bar grinding pressure, 18000 rpm screening wheel speed, 1.9 mm jet size
b) 6.0 bar grinding pressure, 18000 rpm screening wheel speed, 1.9 mm jet size
c) 8.0 bar grinding pressure, 16000 rpm screening wheel speed, 1.3 mm jet size The micronised preparation obtained is characterised by an average particle size of 1.6 to 1.8 μm and a water content of <1.0-0.5%

B.2) Preparation of the Powder Formulation Containing the Virtually Anhydrous Micronised Tiotropium Bromide According to the Invention Apparatus
The following machines and equipment may be used, for example, for preparing the inhalable powder containing the micronised tiotropium bromide according to the invention:

Mixing container or powder mixer:
Gyrowheel mixer 200 L; type: DFW80N-4; manufacturer: Engelsmann, D-67059 Ludwigshafen.

Screening granulator:
Quadro Comil; type: 197-S; manufacturer: Joisten & Kettenbaum, D-51429 Bergisch-Gladbach.

B.2.1) Powder Mixture A

To prepare the powder mixture 299.41 g excipient and 0.59 g virtually anhydrous micronised tiotropium bromide are used. In the 300 g inhalable powder obtained therefrom, the proportion of active substance is 0.2% (based on tiotropium).

Approx. 40-45 g excipient are added to a suitable mixing container through a hand-held screen with a mesh size of 0.315 mm. Then micronised tiotropium bromide in batches of approx. 90-110 mg and excipient in batches of about 40-45 g are screened in alternately in layers. The excipient and the active substance are added in 7 and 6 layers, respectively.

The constituents screened in are then mixed (mixing: 900 rpm). The finished mixture is passed through a hand-held screen twice more and mixed each time (mixing: 900 rpm).

Using the procedure described in Example 1 it is possible to obtain inhalable powders of the kind that can be packed into corresponding plastic capsules to produce inhalation capsules as specified below:

Example 2.1.1

| | |
|---|---|
| micronised tiotropium bromide: | 0.0109 mg |
| lactose monohydrate*): | 5.4891 mg |
| polyethylene capsules: | 100.0 mg |
| Total: | 105.5 mg |

*)the excipient is characterised by the following parameters:
average particle size: 17.9 μm;
10% fine content: 2.3 μm;
specific surface: 0.61 m$^2$/g;

Example 2.1.2

| | |
|---|---|
| micronised tiotropium bromide: | 0.0109 mg |
| lactose monohydrate*): | 5.4891 mg |
| polyethylene capsules: | 100.0 mg |
| Total: | 105.5 mg |

*)the excipient is characterised by the following parameters:
average particle size: 18.5 μm;
10% fine content: 2.2 μm;
specific surface: 0.83 m$^2$/g;

Example 2.1.3

| | |
|---|---|
| micronised tiotropium bromide: | 0.0109 mg |
| lactose monohydrate*): | 5.4891 mg |
| polyethylene capsules: | 100.0 mg |
| Total: | 105.5 mg |

*)the excipient is characterised by the following parameters:
average particle size: 21.6 μm;
10% fine content: 2.5 μm;
specific surface: 0.59 m$^2$/g;

Example 2.1.4

| | |
|---|---|
| micronised tiotropium bromide: | 0.0109 mg |
| lactose monohydrate*): | 5.4891 mg |
| polyethylene capsules: | 100.0 mg |
| Total: | 105.5 mg |

*)the excipient is characterised by the following parameters:
average particle size: 16.0 μm;
10% fine content: 2.0 μm;
specific surface: 0.79 m$^2$/g;

Example 2.1.5

| | |
|---|---|
| micronised tiotropium bromide: | 0.0217 mg |
| lactose monohydrate*): | 5.4783 mg |
| polyethylene capsules: | 100.0 mg |
| Total: | 105.5 mg |

*)the excipient is characterised by the following parameters:
average particle size: 17.9 μm;
10% fine content: 2.3 μm;
specific surface: 0.61 m$^2$/g;

Example 2.1.6

| | |
|---|---|
| micronised tiotropium bromide: | 0.0217 mg |
| lactose monohydrate*): | 5.4783 mg |
| polyethylene capsules: | 100.0 mg |
| Total: | 105.5 mg |

*)the excipient is characterised by the following parameters:
average particle size: 18.5 μm;
10% fine content: 2.2 μm;
specific surface: 0.83 m$^2$/g;

Example 2.1.7

| | |
|---|---|
| micronised tiotropium bromide: | 0.0217 mg |
| lactose monohydrate*): | 5.4783 mg |
| polyethylene capsules: | 100.0 mg |
| Total: | 105.5 mg |

*)the excipient is characterised by the following parameters:
average particle size: 21.6 μm;
10% fine content: 2.5 μm;
specific surface: 0.59 m$^2$/g;

Example 2.1.8

| | |
|---|---|
| micronised tiotropium bromide: | 0.0217 mg |
| lactose monohydrate*): | 5.4783 mg |
| polyethylene capsules: | 100.0 mg |
| Total: | 105.5 mg |

*) the excipient is characterised by the following parameters:
average particle size: 16.0 μm;
10% fine content: 2.0 μm;
specific surface: 0.79 m$^2$/g;

Example 2.1.9

| | |
|---|---|
| micronised tiotropium bromide: | 0.0054 mg |
| lactose monohydrate*): | 5.4944 mg |
| polyethylene capsules: | 100.0 mg |
| Total: | 105.5 mg |

*) the excipient is characterised by the following parameters:
average particle size: 17.9 μm;
10% fine content: 2.3 μm;
specific surface: 0.61 m$^2$/g;

Example 2.1.10

| | |
|---|---|
| micronised tiotropium bromide: | 0.0054 mg |
| lactose monohydrate*): | 5.4946 mg |
| polyethylene capsules: | 100.0 mg |
| Total: | 105.5 mg |

*)the excipient is characterised by the following parameters:
average particle size: 18.5 μm;
10% fine content: 2.2 μm;
specific surface: 0.83 m$^2$/g;

Example 2.1.11

| | |
|---|---|
| micronised tiotropium bromide: | 0.0054 mg |
| lactose monohydrate*): | 5.4946 mg |
| polyethylene capsules: | 100.0 mg |
| Total: | 105.5 mg |

*) the excipient is characterised by the following parameters:
average particle size: 21.6 μm;
10% fine content: 2.5 μm;
specific surface: 0.59 m$^2$/g;

Example 2.1.12

| | |
|---|---|
| micronised tiotropium bromide: | 0.0054 mg |
| lactose monohydrate*): | 5.4946 mg |
| polyethylene capsules: | 100.0 mg |
| Total: | 105.5 mg |

*)the excipient is characterised by the following parameters:
average particle size: 16.0 μm;
10% fine content: 2.0 μm;
specific surface: 0.79 m$^2$/g;

Example 2.1.13

| | |
|---|---|
| micronised tiotropium bromide: | 0.0054 mg |
| lactose monohydrate*): | 9.9946 mg |
| polyethylene capsules: | 100.0 mg |
| Total: | 110.0 mg |

*)the excipient is characterised by the following parameters:
average particle size:  17.9 μm;
10% fine content:  2.3 μm;
specific surface:  0.61 m$^2$/g;

Example 2.1.14

| | |
|---|---|
| micronised tiotropium bromide: | 0.0109 mg |
| lactose monohydrate*): | 9.9891 mg |
| polyethylene capsules: | 100.0 mg |
| Total: | 110.0 mg |

*)the excipient is characterised by the following parameters:
average particle size:  18.5 μm;
10% fine content:  2.2 μm;
specific surface:  0.83 m$^2$/g;

Example 2.1.15

| | |
|---|---|
| micronised tiotropium bromide: | 0.0217 mg |
| lactose monohydrate*): | 9.9783 mg |
| polyethylene capsules: | 100.0 mg |
| Total: | 105.5 mg |

*)the excipient is characterised by the following parameters:
average particle size:  18.5 μm;
10% fine content:  2.2 μm;
specific surface:  0.83 m$^2$/g;

B.2.2) Powder Mixture B

In the following Examples lactose-monohydrate (200M) is used as the coarser excipient. This may be obtained for example from DMV International, 5460 Veghel/NL under the product title Pharmatose 200M.

In the Examples which follow, lactose-monohydrate (5μ) is used as the finer excipient. It may be obtained from lactose-monohydrate 200M by conventional methods (micronising). Lactose-monohydrate 200M may be obtained, for example, from DMV International, 5460 Veghel/NL, under the product name Pharmatose 200M.

B.2.2.1.) Preparation of the Excipient Mixture 31.82 kg of lactose monohydrate for inhalation (200M) are used as the coarser excipient component. 1.68 kg of lactose monohydrate (5 μm) are used as the finer excipient component. In the resulting 33.5 kg of excipient mixture the proportion of the finer excipient component is 5%.

About 0.8 to 1.2 kg of lactose monohydrate for inhalation (200M) are added to a suitable mixing container through a suitable granulating sieve with a mesh size of 0.5 mm. Then alternate layers of lactose monohydrate (5 μm) in batches of about 0.05 to 0.07 kg and lactose monohydrate for inhalation (200M) in batches of 0.8 to 1.2 kg are sieved in. Lactose monohydrate for inhalation (200M) and lactose monohydrate (5 μm) are added in 31 and 30 layers, respectively (tolerance: ±6 layers).

The ingredients sieved in are then mixed together (mixing at 900 rpm).

B.2.2.2) Preparation of the Final Mixture

To prepare the final mixture, 32.87 kg of the excipient mixture (2.1) and about 0.125 kg of the virtually anhydrous micronised tiotropium bromide according to the invention are used. The content of active substance in the resulting 33.0 kg of inhalable powder is 0.38%.

About 1.1 to 1.7 kg of excipient mixture (B.2.1) are added to a suitable mixing container through a suitable granulating sieve with a mesh size of 0.5 mm. Then alternate layers of micronised tiotropium bromide in batches of about 0.0029 kg and excipient mixture (B.2.1) in batches of 0.6 to 0.8 kg are sieved in. The excipient mixture and the active substance are added in 46 and 45 layers, respectively (tolerance: ±9 layers).

The ingredients sieved in are then mixed together (mixing at 900 rpm). The final mixture is passed through a granulating sieve twice more and then mixed (mixing at 900 rpm).

Inhalation capsules having the following composition were produced using the mixture obtained according to B.2.2.2 or with mixtures obtained analogously:

Example 2.2.3

| | |
|---|---|
| micronised tiotropium bromide: | 0.0217 mg |
| lactose monohydrate (200 M): | 5.2029 mg |
| lactose monohydrate (5 μm): | 0.2754 mg |
| hard gelatine capsule: | 49.0 mg |
| Total: | 54.5 mg |

Example 2.2.4

| | |
|---|---|
| micronised tiotropium bromide: | 0.0217 mg |
| lactose monohydrate (200 M): | 4.9279 mg |
| lactose monohydrate (5 μm): | 0.5504 mg |
| hard gelatine capsule: | 49.0 mg |
| Total: | 54.5 mg |

Example 2.2.5

| | |
|---|---|
| micronised tiotropium bromide: | 0.0217 mg |
| lactose monohydrate (200 M): | 5.2029 mg |
| lactose monohydrate (5 μm): | 0.2754 mg |
| polyethylene capsule: | 100.0 mg |
| Total: | 105.50 mg |

C) Measuring Techniques for Determining the Particle Sizes of the Excipient Components Used in B)

The following describes how to determine the average particle size of the different excipient ingredients of the formulation which may be obtained according to B), containing the virtually anhydrous micronised tiotropium bromide according to the invention.

C.1) Determining the Particle Size of Finely Divided Lactose

Measuring Equipment and Settings:

The equipment is operated according to the manufacturer's instructions.

| Measuring equipment: | HELOS Laser-diffraction spectrometer, (SympaTec) |
|---|---|
| Dispersing unit: | RODOS dry disperser with suction funnel, (SympaTec) |
| Sample quantity: | from 100 mg |
| Product feed: | Vibri Vibrating channel, Messrs. Sympatec |
| Frequency of vibrating channel: | 40 rising to 100% |
| Duration of sample feed: | 1 to 15 sec. (in the case of 100 mg) |
| Focal length: | 100 mm (measuring range: 0.9-175 µm) |
| Measuring time: | about 15 s (in the case of 100 mg) |
| Cycle time: | 20 ms |
| Start/stop at: | 1% on channel 28 |
| Dispersing gas: | compressed air |
| Pressure: | 3 bar |
| Vacuum: | maximum |
| Evaluation method: | HRLD |

Sample Preparation/Product Feed:

At least 100 mg of the test substance are weighed onto a piece of card.

Using another piece of card all the larger lumps are broken up. The powder is then sprinkled finely over the front half of the vibrating channel (starting about 1 cm from the front edge). After the start of the measurement the frequency of the vibrating channel is varied from about 40% up to 100% (towards the end of the measurement). The time taken to feed in the entire sample is 10 to 15 sec.

C.2) Determining the Particle Size of Lactose 200M

Measuring Equipment and Settings:

The equipment is operated according to the manufacturer's instructions.

| Measuring equipment: | Laser diffraction spectrometer (HELOS), Sympatec |
|---|---|
| Dispersing unit: | RODOS dry disperser with suction funnel, Sympatec |
| Sample quantity: | 500 mg |
| Product feed: | VIBRI Vibrating channel, Messrs. Sympatec |
| Frequency of vibrating channel: | 18 rising to 100% |
| Focal length (1): | 200 mm (measuring range: 1.8-350 µm) |
| Focal length (2): | 500 mm (measuring range: 4.5-875 µm) |
| Measuring time: | 10 s |
| Cycle time: | 10 ms |
| Start/stop at: | 1% on channel 19 |
| Pressure: | 3 bar |
| Vacuum: | maximum |
| Evaluation method: | HRLD |

Sample Preparation/Product Feed:

About 500 mg of the test substance are weighed onto a piece of card.

Using another piece of card all the larger lumps are broken up. The powder is then transferred into the funnel of the vibrating channel. A gap of 1.2 to 1.4 mm is set between the vibrating channel and funnel. After the start of the measurement the amplitude setting of the vibrating channel is increased from 0 to 40% until a continuous flow of product is obtained. Then it is reduced to an amplitude of about 18%. Towards the end of the measurement the amplitude is increased to 100%.

The invention claimed is:

1. A process for preparing virtually anhydrous micronised tiotropium bromide having a water content of ≤1.5% and a characteristic particle size $X_{50}$ of between 1.0 µm and 3.5 µm and a $Q_{(5.8)}$ of more than 60%, comprising:
   comminuting crystalline tiotropium bromide monohydrate particles in a gas jet mill having a grinding function and a sifting function and also comminuting the tiotropium bromide monohydrate particles in a fluidized powder bed wherein the particles are accelerated in free flow, such that the comminuting is conducted in a single current that is countercurrent to the gas jet mill.

2. The process according to claim 1, wherein the crystalline tiotropium bromide monohydrate is characterised by an endothermic peak at 230±5° C. (at a heating rate of 10K/min) occurring during thermal analysis using DSC.

3. The process according to claim 1, wherein the virtually anhydrous micronised tiotropium bromide has a water content of ≤1.2%.

4. The process according to claim 1, wherein the virtually anhydrous micronised tiotropium bromide has a characteristic particle size $X_{50}$ of between 1.1 µm and 3.3 µm and a $Q_{(5.8)}$ of more than 70%.

5. The process according to claim 1, wherein the gas jet mill uses a grinding gas that is air, dehumidified air, fractionated air, noble gases or nitrogen.

6. The process according to claim 1, wherein grinding pressure during the grinding process is adjusted to a value of 2-10 bar.

7. The process according to claim 1, wherein the gas jet mill has more than one grinding jet, with at least two grinding jets directed towards one another, and at least one grind jet has a jet diameter of 1.3-2.5 mm.

8. The process according to claim 1, wherein the sifting function in the grinding process is carried out by a screening wheel at a screening wheel speed of 5000-22000 revolutions per minute.

9. Virtually anhydrous micronised tiotropium bromide made by a process according to claim 1, wherein the virtually anhydrous micronised tiotropium bromide has a water content of ≤1.5% and a characteristic particle size $X_{50}$ of between 1.0 µm and 3.5 µm and a $Q_{(5.8)}$ of more than 60% and is characterized by an X-ray powder diagram having values of d=5.66 Å; 5.03 Å; and 3.99 Å.

10. A medicament containing virtually anhydrous micronised tiotropium bromide, made by a process according to claim 1, wherein the virtually anhydrous micronised tiotropium bromide has a water content of ≤1.5% and a characteristic particle size $X_{50}$ of between 1.0 µm and 3.5 µm and a $Q_{(5.8)}$ of more than 60% and is characterized by an X-ray powder diagram having values of d=5.66 Å; 5.03 Å; and 3.99 Å.

11. The medicament according to claim 10, characterised in that it is an inhalable powder.

12. The inhalable powder according to claim 11, characterised in that it contains at least about 0.029% of virtually anhydrous micronised tiotropium bromide in admixture with a physiologically acceptable excipient.

13. The inhalable powder according to claim 12, characterised in that monosaccharides, disaccharides, oligo- and polysaccharides, polyalcohols, salts or mixtures of these excipients with one another as used as the excipients.

14. The inhalable powder according to claim 13, characterised in that glucose, arabinose, lactose, saccharose, maltose, trehalose, dextrane, sorbitol, mannitol, xylitol, sodium chloride, calcium carbonate or mixtures of these excipients with one another as used as the excipients.

15. The inhalable powder according to claim 11 or 12, characterised in that it also contains at least one active substance selected from among the betamimetics, corticosteroids, PDE4-inhibitors, LTD4-antagonists, EGFR-inhibitors, dopamine agonists, H1-antihistamines and PAF-antagonists.

16. A method for the treatment of respiratory complaints in a patient in need thereof, comprising administering to the patient virtually anhydrous micronised tiotropium bromide according to claim 9.

17. A method for the treatment of asthma or COPD in a patient in need thereof, comprising administering to the patient virtually anhydrous micronised tiotropium bromide according to claim 9.

18. The process of claim 1, wherein the prepared virtually anhydrous micronised tiotropium bromide has a water content of ≤1.0%.

19. The virtually anhydrous micronised tiotropium bromide of claim 9, which has a water content of <1.0%.

20. The medicament of claim 10, wherein the virtually anhydrous micronised tiotropium bromide has a water content of <1.0%.

\* \* \* \* \*